US007645463B2

(12) United States Patent
Wu (10) Patent No.: US 7,645,463 B2
(45) Date of Patent: Jan. 12, 2010

(54) METHOD FOR TREATING DIABETIC VASCULAR COMPLICATIONS

(75) Inventor: Rong-Tsun Wu, Taipei (TW)

(73) Assignee: National Yang-Ming University, Taipei (TW)

( * ) Notice: Subject to any disclaimer, the term of this patent is extended or adjusted under 35 U.S.C. 154(b) by 167 days.

(21) Appl. No.: 11/582,894

(22) Filed: Oct. 18, 2006

(65) Prior Publication Data

US 2008/0008775 A1 Jan. 10, 2008

Related U.S. Application Data

(60) Provisional application No. 60/804,656, filed on Jun. 14, 2006.

(51) Int. Cl.
*A61K 36/894* (2006.01)
(52) U.S. Cl. ...................................... 424/725
(58) Field of Classification Search ........................ None
See application file for complete search history.

(56) References Cited

U.S. PATENT DOCUMENTS 5,019,580 A * 5/1991 Iwu ............................ 514/299

OTHER PUBLICATIONS

Bell et al.: High Fructose Feeding of Streptozotocin-Diabetic Rats is Associated With Increased Cataract Formation and Increased Oxidative Stress in the Kidney.: British Journal of Nutrition. (2000), 84, 575-582.*
Herzberg et al.: Conflicting Results Obtained by RAPD-PCR and Large Subunit RDNA Sequences in Determining and Comparing Yeast Strainss Isolated From Flowers: A Comparison of Two Methods.: International Journal of Systematic and Evolutionary Microbiology (2002), 52, 1423-1433.*
Retrieved from the internet ,http://en.wikipedia.org/wiki/Dioscorea>. retrieved on Feb. 2, 2008.*
R. Singh, et al., "Advanced glycation end-products: a review," Diabetologia 44: 129-146 (2001).
Helen Vlassaria, et al., "Exogenous advanced glycosylation end products induce complex vascular dysfunction in normal aminals: A model for diabetic and aging complications," Proc. Natl. Acad. Sci. USA, vol. 89, pp. 12043-12047, Dec. 1992.
H. Vlassaria, et al., "Diabetes and advanced glycation endproducts," Journal of Internal Medicine (2002); 251: 87-101.

* cited by examiner

*Primary Examiner*—Patricia Leith
*Assistant Examiner*—Melenie McCormick
(74) *Attorney, Agent, or Firm*—Panitch Schwarze Belisario & Nadel LLP (57) ABSTRACT

The present invention provides a method for treating diabetic vascular complications including administering to a subject in need thereof a therapeutically effective amount of an extract product of a *Dioscorea* species. The extract product preferably is prepared by a process which involves (a) extracting a tuber of the *Dioscorea* species with an alcohol-based solvent in the presence of an acetic acid solution to form an extract composition, (b) subjecting a resultant product obtained in step (a) to obtain a soluble fraction, and (c) removing solvent from the soluble fraction obtained in step (b) to obtain the extract product.

6 Claims, 8 Drawing Sheets

METHOD FOR TREATING DIABETIC VASCULAR COMPLICATIONS

CROSS-REFERENCE TO RELATED APPLICATION

This application claims the benefit of U.S. Provisional Patent Application No. 60/804,656, filed Jun. 14, 2006, the disclosure of which is hereby incorporated herein by reference in its entirety.

BACKGROUND OF THE INVENTION

The present invention relates to a medical treatment of diabetic vascular complications, and particularly to a method for treating diabetic vascular complications with an extract product of a *Dioscorea* species.

Non-enzymatic glycation (Maillard reaction) has been implicated in the pathogenesis of diabetic vascular complications. Recent immunohistochemical studies have shown that the formation of advanced glycation end product (AGE) is enhanced in diabetic subjects (Liu et al., Diabetes. 48: 2074-2082, 1999). AGE formation per se is known to alter the structural and functional properties of the tissue protein. In addition, the interaction between AGE-modified proteins and various types of cells is thought to play a pathological role in the abnormalities observed in diabetic subjects. Therefore, an excessive accumulation of AGE in the body has been suggested as a main factor for triggering diabetic vascular complications such as atherosclerotic lesions, nephropathy, vessel injury, neuropathy and retinopathy (Vlassara et al., Journal of Internal Medicine 251: 87-101, 2002).

Chronic hyperglycemia is essentially involved in the development and progression of diabetic vascular complications. In the liver, endocytosis of AGE-modified protein leads to loss of scavenger receptors and delayed intracellular transport in hepatic sinusoidal endothelial cells. (Hansen et al., Diabetologia 45:1379-1388, 2002) In the kidney, AGE-modified type IV collagen and laminin reduce their ability to interact with negatively charged proteoglycans, increasing vascular permeability to albumin. (Silbiger et al., Kidney Int 43: 853-64, 1993)

To date, there have been several approaches which seek to prevent AGE formation, reduce AGE effects on cells and break pre-existing AGE crosslinks. An important pharmacological strategy has utilized the small nucleophilic hydrazine compound aminoguanidine, a potent inhibitor of AGE-mediated crosslinking. Another AGE-inhibiting drug is still under development including the thiazolidine derivative OPB-9195 which has been shown to prevent the progression of diabetic glomerulosclerosis in rats. An angiotensin converting enzyme inhibitor (ACEI), such as rampril has also been found to alleviate the nephropathy in diabetic mice treated with streptozotocin (STZ).

Although the compounds or drugs developed so far have been directed to inhibit formation of AGE and AGE crosslinking, the existing AGE is not cleared by the specific compounds or the drugs remain to damage the cells and tissues in the diabetic subject. It is also difficult to establish the toxicity and side effects associated with the compounds or drugs administered in the diabetic subject.

*Dioscorea* is one of the very important pharmaceutical plants used in traditional Chinese medicine, and the medicinal effects thereof have been studied for years. In 1936, Tsukamoto et al isolated diosgenin, a steroid saponin of *Dioscorea*, from the Dioscoreacea family of plants and used the isolated diosgenin as a raw material for rapid synthesis of medicinal steroids. However, no study has yet been conducted using an extract product of *Dioscorea* in the treatment of diabetic vascular complications.

BRIEF SUMMARY OF THE INVENTION

The invention relates to a method for treating a diabetic vascular complication, which comprises administering to a subject in need thereof a therapeutically effective amount of an extract product of a *Dioscorea* species.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise experimental conditions and parameters associated with the drawings.

In the drawings.

DETAILED DESCRIPTION OF THE INVENTION

For a better understanding of the present invention, some of the terms used herein are explained in more detail.

The articles "a" and "an" are used herein to refer to one or more than one (i.e., at least one) of the grammatical object of the article. By way of example, "an element" means one element or more than one element.

The term "diabetic vascular complication" used herein refers to a vascular disorder that arises during the course of diabetes mellitus, including cardiovascular disease, neuropathy, retinopathy and nephropathy, which could account for disabilities and high mortality rates in diabetic patients.

As used herein, "percent" or "%" means percent by weight of the component with which it is used based on the weight of the composition of which the component is a part.

As used herein, a "subject" is any animal that is or may be affected by diabetic vascular complications, such as mammals and specifically including humans.

The present invention provides a method for treating a diabetic vascular complication comprising administering to a subject in need thereof a therapeutically effective amount of an extract product of a *Dioscorea* species. In an example of the invention, the extract product of the *Dioscorea* species is prepared by a process comprising the steps of:

(a) mixing a tuber of the *Dioscorea* species with an alcohol-based solvent in the presence of acetic acid to obtain an extract composition;

(b) subjecting the extract composition obtained in step (a) to a separating treatment to obtain a soluble fraction; and (c) removing the solvent from the soluble fraction obtained in step (b) to obtain the extract product of the *Dioscorea* species.

The alcohol-based solvent includes any suitable alcohol capable of acting as a solvent. For example, without limitation, the alcohol-based solvent comprises methanol, ethanol, isopropanol or butanol, or a mixture thereof. In accordance with one embodiment, the tuber of the *Dioscorea* species is extracted with ethanol in the presence of about 1% acetic acid solution. Preferably, the tuber of the *Dioscorea* species is extracted with about 50 to about 90% ethanol in the presence of about 1% acetic acid solution. In one embodiment of the invention, the tuber of the *Dioscorea* species is extracted with about 85% ethanol in the presence of about 1% acetic acid solution. In accordance with another embodiment, the tuber of the *Dioscorea* species is ground and mixed with about 30% to about 90% methanol (such as about 40% methanol), in the presence of about 1% acetic acid solution. The extracted mixture may be allowed to stand overnight and separated by a filtering step to obtain a filtrate, such as vacuum filtering. The filtrate may be then lyophilized to obtain the crude extract of the *Dioscorea*.

In one example of the invention, the method optionally comprises prior to step (a) of the preparation process, a preliminary treatment of the tuber of the *Dioscorea* species including the steps of:

(i) immersing the tuber of the *Dioscorea* species in an about 1% acetic acid solution;

(ii) grinding the tuber of *Dioscorea* species; and (iii) lyophilizing the ground and acetic acid-treated tuber of the *Dioscorea* species to produce a ground, lyophilized and acetic acid-treated tuber of the *Dioscorea* species.

In accordance with an embodiment of the invention, the extract product of the *Dioscorea* species may be prepared by immersing the tuber of the *Dioscorea* species in an about 1% acetic acid solution, followed by the steps of grinding and then lyophilizing the acetic acid treated tuber and then extracting the lyophilized tuber by immersing with an alcohol-based solvent, and mixing the ground lyophilized tuber with an alcohol-based solvent to form a mixture, and allowing the mixture to stand overnight to obtain the extract product.

The present invention also provides a method for treating diabetic vascular complications. The method comprises administering to a subject in need of such treatment a therapeutically effective amount of an extract product of the *Dioscorea* species, wherein the extract product is prepared by a process comprising the steps of:

(a) immersing a tuber of the *Dioscorea* species in a 1% acetic acid solution;

(b) grinding the acetic acid-treated tuber of the *Dioscorea* species;

(c) lyophilizing the ground and acetic acid-treated tuber of the *Dioscorea* species; to produce a ground, lyophilized and, acetic acid-treated tuber of the *Dioscorea* species;

(d) mixing at least a portion of the ground, lyophilized and acetic acid-treated tuber of the *Dioscorea* species of step (c) with an alcohol-based solvent in a presence of an about 1% acetic acid solution to obtain an extract composition;

(e) subjecting the extract composition obtained in step (d) to a separating treatment to obtain a soluble fraction; and (f) removing the solvent from the soluble fraction obtained in step (e) to obtain the extract product of the *Dioscorea* species.

According to one embodiment of the invention, the *Dioscorea* species used in the preparation process and treatment method of this invention is *Dioscorea alata* L. cv. Phyto, characterized by a randomly amplified polymorphic DNA (RAPD) fingerprint comprising the following 14 DNA bands when the genomic DNA of the *Dioscorea* species is amplified with a primer of SEQ ID NO: 9: 428 bp, 452 bp, 537 bp, 602 bp, 723 bp, 817 bp, 934 bp, 1140 bp, 1242 bp, 1478 bp, 1641 bp, 1904 bp, 2151 bp and 2918 bp. The randomly amplified polymorphic DNA (RAPD) analysis is described in Example 4.

In accordance with one embodiment, a therapeutically effective amount of the extract product of the *Dioscorea* species is administered via an oral route to the subject in need of a treatment of a diabetic vascular complication. However, the extract product may be administered to the subject in need thereof in any other appropriate administration route to achieve similar therapeutic effects, for example, intravenous, intraperitoneal, transdermal routes, particularly a transmucosal route including a nasal route.

For those skilled in the art, the therapeutically effective amount, as well as dosage and frequency of administration, may easily be determined according to their knowledge and standard methodology of merely routine experimentation based on the present disclosure. The dosage may be about 1 to about 100 mg/kg body weight/day, preferably about 5 to about 40 mg/kg body weight/day, and most preferably about 10 to about 30 mg/kg body weight/day.

The following examples are provided to further illustrate the present invention. The examples are not intended to limit the scope of the present invention and they should be so interpreted.

EXAMPLES OF THE INVENTION

Example 1

Preparation of Crude Extract (PH) of *Dioscorea* Species

Peeled tubers of *Dioscorea* species were immersed in an alcohol-based solution in the presence of 1% acetic acid. After stirring, the mixture solution was allowed to stand overnight. The soluble portion obtained from the process was lyophilized to yield a crude extract (PH) of the *Dioscorea* species.

Specifically, 1.4 kg of the peeled tubers of *Dioscorea* species were cut into cubes and immersed in a 1% acetic acid solution. The cubes were immersed in the acetic acid solution overnight and supernatant was removed. The cubes were lyophilized before the extraction.

The lyophilized cubes were ground and mixed with about 30% to about 90% methanol (such as about 40% methanol) as a solvent of about 1.5 L to about 2.5 L, in the presence of about 1% acetic acid solution. The mixture was stood overnight and filtered by vacuum filtering to obtain a filtrate. The filtrate was then lyophilized to obtain the crude extract (PH) of the *Dioscorea* species.

Alternatively, the lyophilized cubes were ground and mixed with about 50 to about 90% ethanol (such as about 85% ethanol) as a solvent of about 1.5 to about 2.5 L, in the presence of about 1% acetic acid solution. Similarly, the mixture stood overnight and filtered by vacuum filtering to obtain a filtrate. The filtrate was then lyophilized to obtain the crude extract (PH) of the *Dioscorea* species.

Example 2

Analysis of the Crude Extract (PH) of *Dioscorea* Species

The crude extracts (including methanol and ethanol extracts) obtained from Example 1 were analyzed by HPLC using a Shimadzu HPLC system (Class VP series with Class VP 6.12 version software; Shimadzu, Kyoto, Japan) with two pumps (LC-10AT), an SPD-10A variable wavelength-programmable UV/Vis photodiode array detector, an SCL-10A system controller and a C-18 column (Supelcosil, 250 mm×4.6 mm, and with 5 μm packing; Supelco, Bellefonte, USA) fitted with a guard column (35 mm×4.6 mm, and with 5 μm packing; Supelco).

The HPLC samples of PH (10 mg/mL) were prepared using a mobile phase containing 88% water (Mobile Phase A) and 12% methyl alcohol (Mobile Phase B) into aliquots of 20 μL and loaded to the column equilibrated with the mobile phase at a flow rate of 0.9 mL/min. All the organic solvents were of HPLC grade, filtered with a 0.22 μm filter and degassed prior to use. The total run time of the HPLC method was set at 20 min. The elution profile was monitored on the Shimadzu SPD-10A UV-Vis photodiode array detector at 260 nm. The results were quantified based on the following parameters listed in Table 1 below. The chromatograms as resulted were processed and recorded with Class VP 6.12 version software (Shimadzu, Kyoto, Japan).

TABLE 1

| EVENT | TIME | VALUE |
| --- | --- | --- |
| WIDTH | 0 | 5 |
| SLOPE | 0 | 200 |
| DRIFT | 0 | 0 |
| T. DBL | 0 | 1000 |
| NEGATIVE PEAK ON | 0 | 0 |
| TAILING ON | 0 | 0 |

Figure 1A:
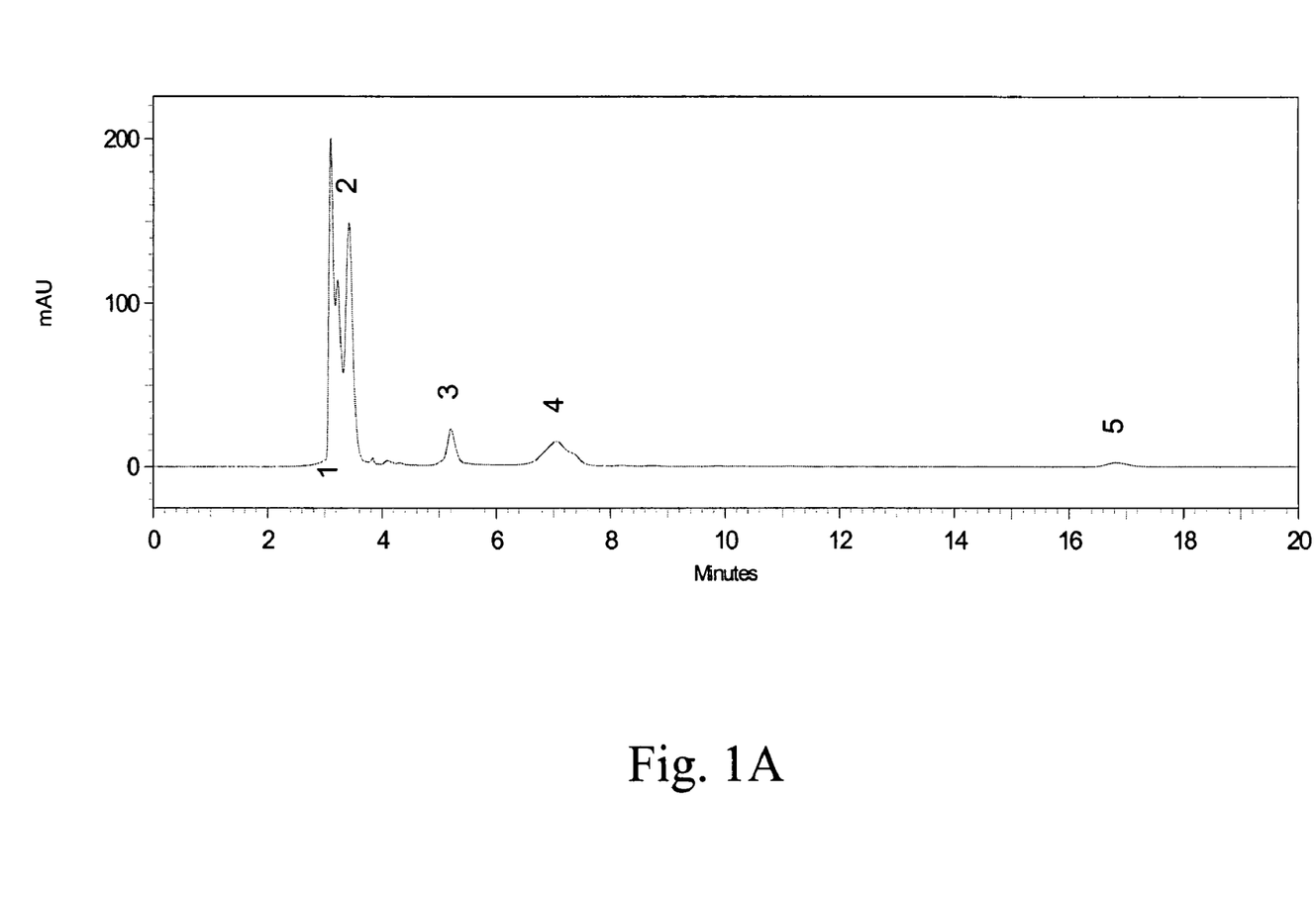
FIGS. 1A and 1B are chromatograms showing peaks generated by HPLC analysis of methanol and ethanol extracts of *Dioscorea* species, respectively.
Figure 1B:
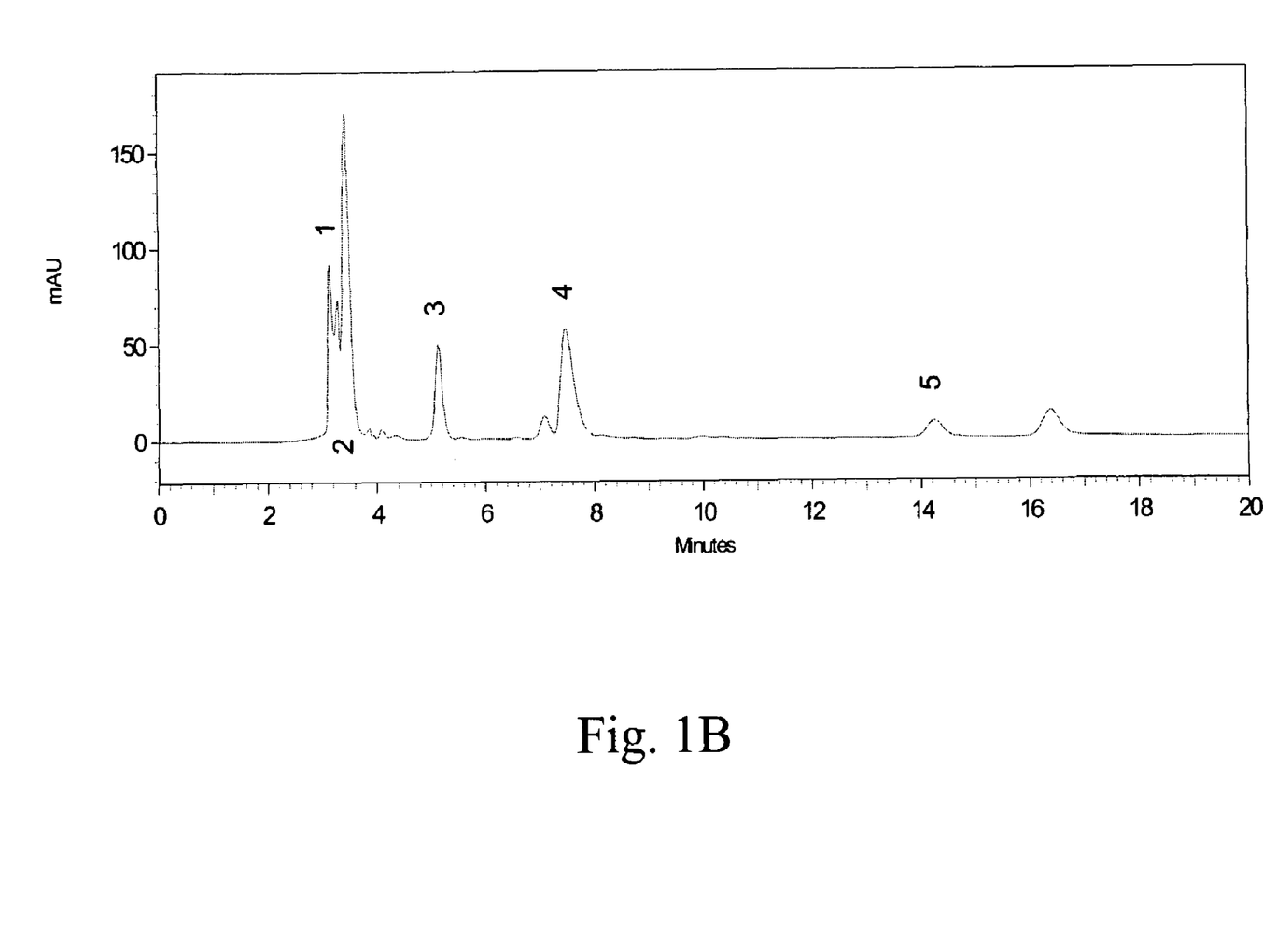

Referring to both FIGS. 1A and 1B, the peaks in the profiles were well resolved. There were several peaks observed in the profiles, where the peak 4 shows the active ingredient in PH. As shown in FIGS. 1A and 1B, the retention time for the peak 4 was about 7.045 min for the methanol extract and was about 7.474 for the ethanol extract. Therefore, the HPLC profile of the methanol extract of *Dioscorea* species is similar to that of the ethanol extract. The methanol extract of *Dioscorea* species is almost the same as the ethanol extract of *Dioscorea* species in chemical components, and they should provide the same activities and efficacies in treatment.

Example 3

Preparation of Mouse Feed Containing the Crude Extract (PH)

Purina Chow 5001, a commercially available mouse feed, was ground into powder. The lyophilized crude extract PH was added to the ground feed in an amount to replace the same amount of ground feed, to form a feed mixture. The feed mixture was uniformly mixed with distilled water, re-shaped by extrusion molding, baked for 2 min. in a microwave oven at proper power, and refrigerated at −70° C. after cooling to room temperature. After lyophilization, the feed mixture was formed into pellets very similar to those of the original the Purina Chow feed. The pellets were stored in a −20° C. refrigerator. The pellets were warmed to room temperature on the day of feeding, and were sterilized by UV lamp irradiation on a sterile work table. Feed mixtures having different concentrations of the crude extract were prepared.

Example 4

Characterization of *Dioscorea* Species in a Randomly Amplified Polymorphic DNA (RAPD) Analysis DNA Extraction One of the unknown *Dioscorea* species (shown in duplicate as Sample No. 100 or 102) was characterized along with a test panel of 13 known *Dioscorea* species, including *Dioscorea alata* L. cv. (cultivated variety) Tainung No. 1 (Sample No. 1), *Dioscorea esculenta* (Sample No. 3), *Dioscorea bulbifera* (Sample No. 4), *Dioscorea alata* L. cv. 8702 (Sample No. 5), *Dioscorea alata* L. cv. Sanzhi A (Sample No. 6), *Dioscorea alata* L. cv. Sanzhi B (Sample No. 7), *Dioscorea alata* L. cv. Dayeshoufeng (Sample No. 9), *Dioscorea alata* L. cv. Tainung No. 2 (Sample No. 10), *Dioscorea alata* L. cv. Jifa (Sample No. 67), *Dioscorea alata* L. cv. Zhanger No. 2 (Sample No. 64), *Dioscorea alata* L. cv. Dashan No. 3 (Sample No. 13), *Dioscorea alata* L. cv. Dashan No. 2 (Sample No. 12) and *Dioscorea alata* L. cv. Taidong (Sample No. 11), all of which were grown in Taiwan.

For characterzation of the *Dioscorea* species by sequencing, 0.2 g of fresh leaf of each *Dioscorea* sample was collected and ground in a mortar mixed with liquid nitrogen. The ground tissue was mixed with 900 μl of 2% CTAB extraction buffer (containing 1.4 M NaCl, 100 mM Tris-HCl at pH 8.0, 20 mM EDTA and 0.2% β-mercaptoethanol) in a 1.5 ml centrifuge tube, followed by incubating in a 65° C. water bath for 30 minutes. The sample was then centrifuged, and the supernatant was transferred to a clean tube containing 600 μL of chloroform/isoamyl alcohol (24:1) and vortexed until the sample was in an emulsified state. The sample was further centrifuged, and the supernatant was transferred to a clean tube and mixed with 40 μL of 10% CTAB (containing 0.7M NaCl) and 400 μL of chloroform/isoamyl alcohol (24:1). The sample was centrifuged again, and the supernatant (400 μL) was transferred in a clean tube and mixed with 400 μL of CTAB precipitation buffer and left on ice for about 15-20 minutes to precipitate DNA. The DNA sample was rinsed with 400 μL of high-salt TE (10 mM Tris-HCl, pH 8.0; 1 mM EDTA; and 1M NaCl) and 800 μL of 95% ethanol. The DNA sample was centrifuged, and the pellet was further rinsed with 400 μL of 75% ethanol before re-suspending the DNA pellet in distilled and deionized (dd) H$_2$O and stored at −20° C.

RAPD Reaction

A random RAPD primer of SEQ ID NO: 1, in this case OPA-18 (AGGTGACCGT) (Operon Technologies, USA) was used to amplify genomic DNA of the *Dioscorea* species in the RAPD analysis. Polymerase Chain Reaction (PCR) was carried out in a 25 μL volume containing 10× buffer, 2.5 mM of each dNTP (dATP, dCTP, dGTP, and dTTP), 2.0 μM of primer (Operon), 5 units of Taq DNA polymerase (TaKaRa Biomedicals), and 5 ng template DNA. Samples were subjected to 41 cycles consisting of denaturation for 1 min at 94° C., annealing for 1 min at 36° C., extension for 2 min at 72° C., and one final extension cycle at 72° C. for 10 minutes. After completion of the PCR, 10 μL of reaction mixture were loaded into a 2% agarose gel, containing 0.5 μg/mL ethidium bromide for electrophoresis.

Data Analysis

Figure 2:
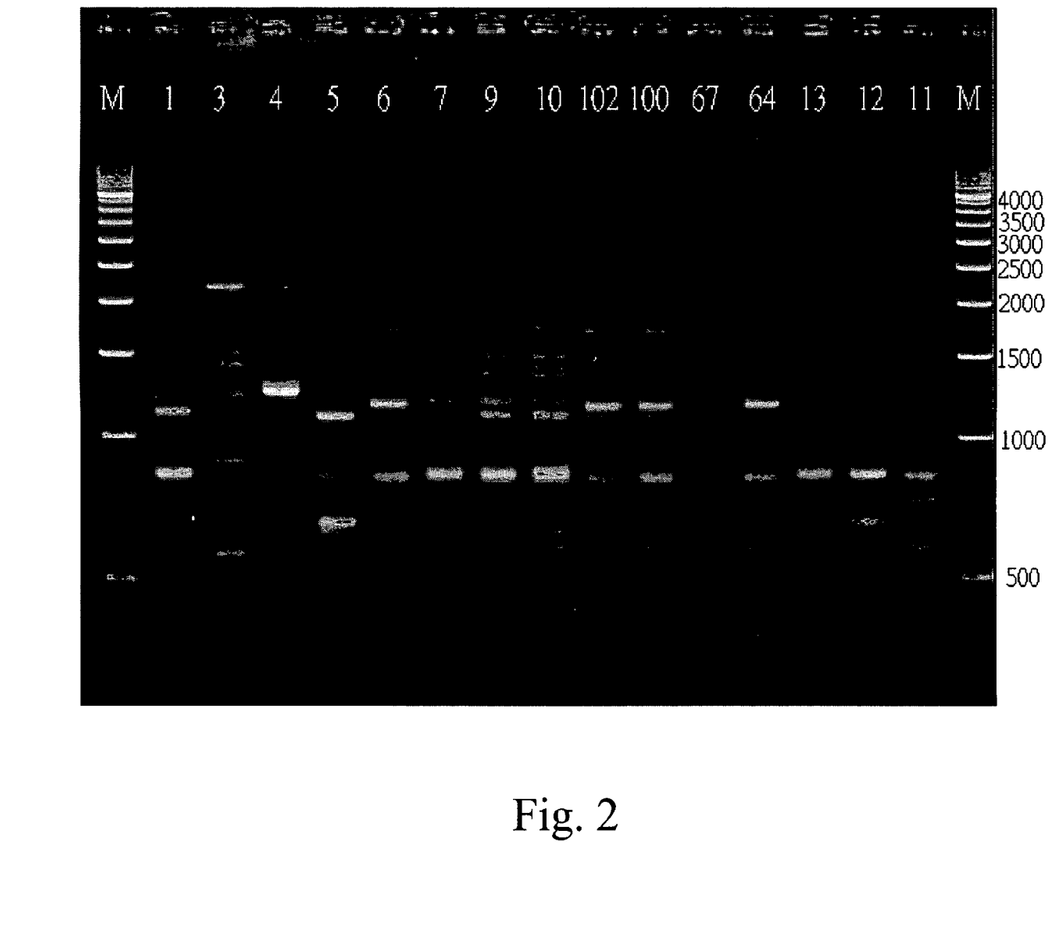
FIG. 2 is a composite image showing electrophoretic marker profiles of amplification products for a test panel of 14 *Dioscorea* species amplified with a single randomly amplified polymorphic DNA (RAPD) primer of SEQ ID NO: 1.

In the gel electrophoresis, both first lane (on the far left) and last lane (on the far right) of the gel were loaded with DNA molecular weight marker (M), such as ΦX174 DNA/HaeIII marker (Promega Co., USA) to provide reference bands of different sizes, such as 500 bp, 1000 bp, 1500 bp, 2000 bp, 2500 bp, 3000 bp, 3500 bp and 4000 bp, followed by loading the PCR sample of each *Dioscorea* species in each lane. The profile of amplified DNA products from each sample was visualized by fluorescent developer and photographic images were captured using an image acquiring software, Alphalmager 1220. Since each *Dioscorea* species from the test panel produced its own DNA bands in the RAPD fingerprint, the RAPD fingerprint of the *Dioscorea* species of the invention was determined to distinguish from other *Dioscorea* species. The fingerprint of the specific *Dioscorea* species comprises the following 14 DNA bands when the genomic DNA of the *Dioscorea* species is amplified with a primer of SEQ ID NO: 9: 428 bp, 452 bp, 537 bp, 602 bp, 723 bp, 817 bp, 934 bp, 1140 bp, 1242 bp, 1478 bp, 1641 bp, 1904 bp, 2151 bp and 2918 bp when genomic DNA of the *Dioscorea* species is amplified with the OPA-18 primer of SEQ ID NO: 1, which is used for characterizing the unknown *Dioscorea* species (shown in duplicate as samples No. 100 or 102 in FIG. 2).

A cluster analysis or pair analysis was also carried out using Gel-Compar software to calculate a similarity index between two *Dioscorea* species. Parameters subjected to the analysis were from RAPD fingerprints. Next, with the unweighted pair-grouping mean arithmetical analysis (UPGMA), the similarity index (F) was calculated in a cluster analysis with the following equation:

$$F = 2n_{xy}/n_x + n_y$$

wherein $n_{xy}$ is the number of common DNA bands in *Dioscorea* species x and y, and $n_x$ and $n_y$ are the total DNA bands in *Dioscorea* species x and y respectively (Nei, M. and W. H. Li. 1979, Mathematical Model for studying genetic variation in terms of restriction endonucleases, Proc. Natl. Acad. Soc. U.S.A. 76: 5269-5273).

The unknown *Dioscorea* species has a similarity index of about 88.9% with *Dioscorea alata* L. cv. Sanzhi A or *Dioscorea alata* L. cv. Zhanger No. 2. Furthermore, the *Dioscorea* species has a similarity index of about 37.5% with *Dioscorea bulbifera* or *Dioscorea esculenta*. Moreover, the unknown *Dioscorea* species has a similarity index of more than 75.5% with *Dioscorea Dioscorea alata* L. cv. Tainung No. 1, *Dioscorea alata* L. cv. 8702, *Dioscorea alata* L. cv. Sanzhi B, *Dioscorea alata* L. cv. Dayeshoufeng, *Dioscorea alata* L. cv. Tainung No. 2, *Dioscorea alata* L. cv. Dashan No. 3 or *Dioscorea alata* L. cv. Dashan No. 2. Based on the cluster analysis or pair analysis results, it was understood that the unknown *Dioscorea* species was different from known species, but more similar to *Dioscorea alata* sub-species. Therefore, the unknown *Dioscorea* species was named as *Dioscorea alata* L. cv. Phyto, as described in U.S. patent application Ser. No. 11/274,775, filed Nov. 15, 2005, U.S. Patent Application Publication No. 20060068036 A1, published Mar. 30, 2006, the disclosure of which is hereby incorporated herein by reference.

Example 5

The Effect of the Crude Extract on in vitro Phagocytosis Assay

Isolation and Culture of Kupffer Cells

C57BL6/j mice were intraperitoneally (ip) injected with a mixture of Rompun® xylazine anesthesia and ketamin (S-(+)-ketamine) anesthesia mixed at a ratio of 1:3. The central vein of each mouse was cannulated with a polyethylene catheter, and the liver tissue was perfused with 10 ml Ca$^{2+}$-free HBSS buffer for 10 minutes at a perfusion rate of 1 ml/min, and HBSS buffer containing 0.05% collagenase type IV for 10 minutes at the perfusion rate of 1 mL/min to soften the liver tissue. The softened liver tissue was excised, rinsed and cut open by a pair of forceps to release cell suspension from the liver tissue. After the connective tissue was detached, the cell suspension was filtered with a #53 nylon mesh and centrifuged at 30 g for 3 minutes. The cell suspension was then centrifuged at 600 g for 5 minutes. The supernatant was discarded and the cell pellet was resuspended in 15 mL RBC lysis buffer and allowed a reaction to take place for 2 minutes. The cell suspension was added with 15 mL of RPMI 1640 medium and centrifuged, and the cell pellet was resuspended in 5 mL of RPMI 1640 medium and layered on top of a Percoll™ solution consisting of 25% (v/v) Percoll™ density gradient medium. The cell solution was centrifuged, and the cell pellet containing enriched Kupffer cells was collected. The enriched Kupffer cells were washed with RPMI 1640 medium and resuspended in serum-free RPMI 1640 medium.

Phagocytosis Assay of Kupffer Cell

Kupffer cells were seeded (4×10$^5$ cells/well) in a 96-well culture plate and cultured in RPMI medium supplemented with 10% FCS, also known as 10% FCS RPMI medium hereinafter, for at least 24 hours. The medium was changed to 2% FCS RPMI medium added with PH of different concentrations (1000 μg/mL, 100 μg/mL, 10 μg/mL and 1 μg/mL). After culturing for 2 hours, 1 μm-sized FITC-beads suspended in 50 μl of PBS were added to each well (5×10$^6$/well) and further cultured at 37° C. for 1.5 hour. Next, the unbounded 1 μm-sized FITC-beads were removed by washing with PBS four times. FluoroQuench™ dye (0.5 μL/well) was added to quench the fluorescence from the ingested 1 μm-sized FITC-beads. The fluorescence of the ingested 1 μm-sized FITC-beads was measured with a cytofluorometer after one hour and normalized with the fluorescence of the control group to determine the relative phagocytosis index as shown in Table 2.

TABLE 2

| Group | Conc. (μg/ml) | Mouse Kupffer cell Ingestion phagocytosis Index |
|---|---|---|
| Control | 2% FCS | 1 |
| Positive control | 100 | 1.01 |

TABLE 2-continued

| Group | Conc. (μg/ml) | Mouse Kupffer cell Ingestion phagocytosis Index |
|---|---|---|
| (Tuftsin) | 10 | 1.2* |
|  | 1 | 1.49** |
| PH | 1000 | 1.17 |
|  | 100 | 1.41** |
|  | 10 | 1.22** |
|  | 1 | 1.25# | a. Data were analyzed by Student's t-test.
*P < 0.05,
P < 0.02,
**P < 0.01

The mouse Kupffer cells treated with crude extract PH of different concentrations (1000 μg/mL, 100 μg/mL, 10 μg/mL and 1 μg/mL) have all shown enhanced ingestion phagocytosis as compared to the control group of the mouse Kupffer cells without any treatment. Different concentrations of tuftsin that can promote Kupffer cell phagocytosis are positive controls in this assay. Therefore, the results suggest that the crude extract of *Dioscorea* has significantly promoted the cellular phagocytosis of the mouse Kupffer cells.

Example 6

Effect of the PH on Expression of the Related Genes

Isolation of Total RNA from the Cells Treated with the PH

Kupffer cells were cultured in a 6-well plate. The culture medium was replaced with serum-free medium and maintained for 4 hours. The cells were treated with PH at concentrations of 100 μg/mL, 10 μg/mL and 1 μg/mL, respectively, for 48 hours. After the treatment with the PH, the cells were harvested and suspended in 1 mL of the Ultraspec™ RNA isolation Kit (Biotex Laboratories Inc. (USA)). The total RNA was obtained by following the standard protocol of the kit. The total RNA obtained was quantitatively determined.

Reverse Transcriptase Polymerase Chain Reaction (RT-PCR) Analysis

The reverse transcription was performed according to the following procedure. The mRNA was first denatured by thermal treatment at 70° C. for 10 minutes in 26.5 μL of DEPC-treated sterilized reaction mixture containing 0.1 μg of oligo-dT, 5 μg of the total RNA. The reverse transcription was performed with 4 μL of 10 mM dNTP, 0.5 μl of rRNasin, 1 μL of AMV (Avian Myeloblastosis virus) reverse transcriptase (RT) (10 units) and 8 μl of 5×RT buffer added to the reaction mixture to come to a total volume of 40 μL, and incubated at 42° C. for 60 minutes, followed by heat inactivation at 90° C. for 5 minutes, and thereby the cDNA products were obtained. Subsequently, 0.5 μL of 10 mM dNTP, 0.5 μL of Prozyme™ DNA polymerase (Protech Enterprise, Taipei, Taiwan) (2 units), 2 μL of 10× Prozyme™ buffer, the primers (1 μL of 1 μg/μL sense DNA and 1 μL of 1 μg/μL antisense DNA) and the sterilized water were added to 2.5 μL of the cDNA products to form a total volume of 20 μL, and incubated in a DNA thermal cycler (Perkin-Elmer-Cetus). Then, the 30-cycles PCR reaction was performed under denaturing temperature 94° C., annealing temperature 50° C. and extension temperature 72° C. The primer sequences including sense and antisense primers for the target genes (mouse CD36, mouse Cathepsin and mouse hepatocyte growth factor (HGF)) are listed in Table 3 below.

TABLE 3

| Primer | Sequence |
|---|---|
| β-actin sense (SEQ ID NO: 2) | 5'-GACTACCTCATGAAGATCCT-3' |
| β-actin antisense (SEQ ID NO: 3) | 5'-CCACATCTGCTGGAAGGTGG-3' |
| Mouse CD36 sense (SEQ ID NO: 4) | 5'-GGATCGAAATCGACCTTAAAG-3' |
| Mouse CD36 antisense (SEQ ID NO: 5) | 5'-TAGCTGGCTTGACCAATATGTT-3' |
| Mouse Cathepsin D sense (SEQ ID NO: 6) | 5'-CGTCTTGCTGCTCATTCTCG-3' |
| Mouse Cathepsin D antisense (SEQ ID NO: 7) | 5'-CCACCAGAAGAGATGTCCCT-3' |
| Mouse HGF sense (SEQ ID NO: 8) | 5'-CCATGAATTTGACCTCTATGA-3' |
| Mouse HGF antisense (SEQ ID NO: 9) | 5'-CTGAGGAATCTCACAGACTTC-3' |

Figure 3:
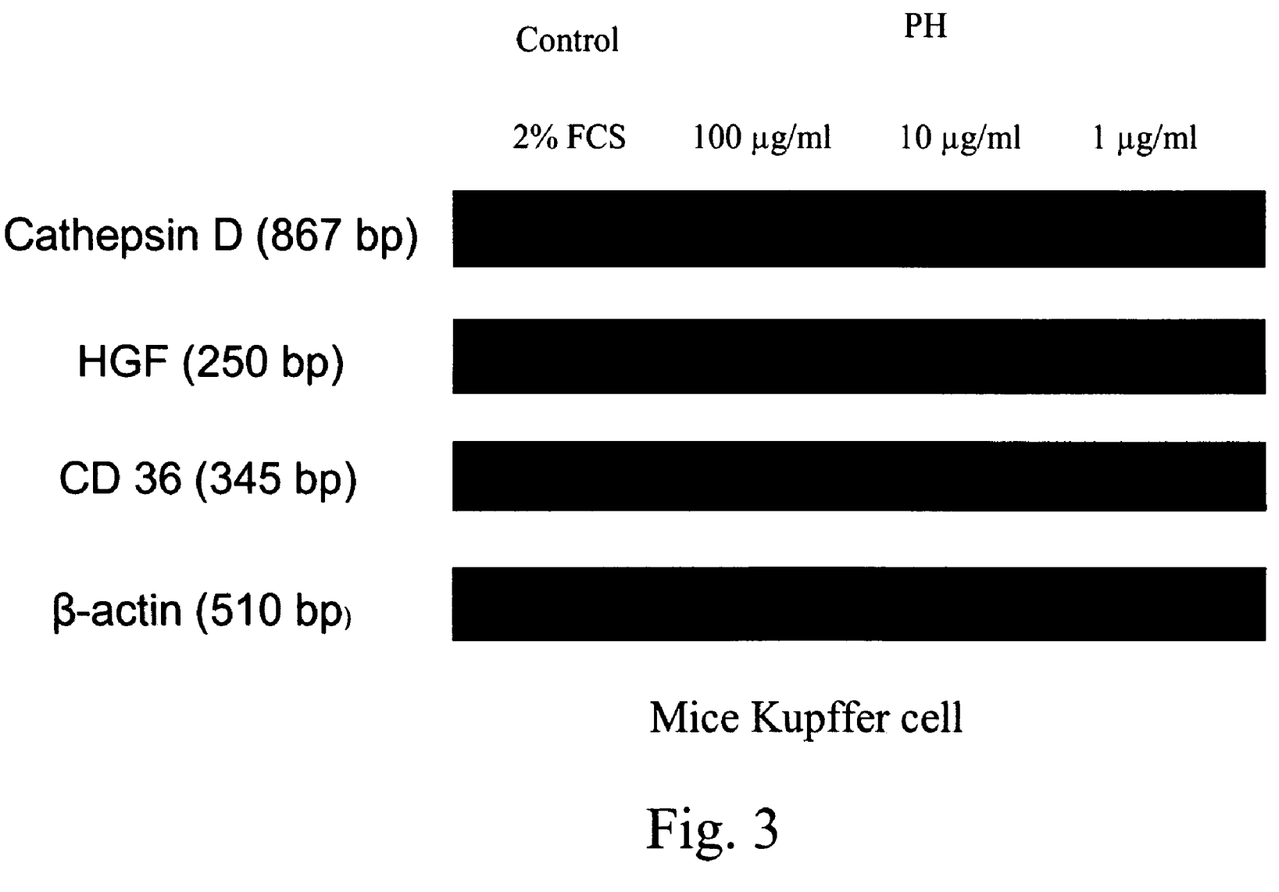
FIG. 3 is a composite image showing a series of gene expressions in Kupffer cells.

CD36 is a Type B scavenger receptor which binds to the known AGEs (Vlassara et al., Journal of Internal Medicine 251: 87-101, 2002). Cathepsin D is an acidic lysosomal protease which degrades the AGEs (Miyata et al., The Journal of Biological Chemistry 272 (7): 4037-4042, 1997). HGF is produced in the liver by Kupffer cells, and is a growth factor that facilitates the functions of hepatocytes. (Lalani et al., International Journal of Molecular Medicine 15: 811-817, 2005). In determining the effect of the crude extract PH, the expression patterns of the CD36 gene (345 bp) (referring to Gene Bank Number (Accession): NM_007643, defined as Gene *Mus musculus* CD36 antigen (Cd36), mRNA, and designed according to the disclosures in Shore et al., Nucleic Acid Reasearch, 30(8): 1767-1773, 2002), Cathepsin D gene (867 bp) (referring to Gene Bank Number (Accession): BC54758, definded as *Mus musculus* cathepsin D, mRNA, complete cds.) and HGF gene (250 bp) (referring to Gene Bank Number (Accession): NM_010427.2, defined as *Mus musculus* hepatocyte growth factor (HGF), mRNA, and designed according to the disclosure in Ikari et al., Developmental Dynamics 228: 173-184, 2003) were evaluated in the Kupffer cells, while the expression of β-actin gene (510 bp) (referring to Gene Bank Number (Accession): NM_007393, defined as *Mus musculus* actin, beta, cytiplasmic (Actb), mRNA) was provided as an internal control. As shown in FIG. 3, the crude extract has increased the expression of Cathepsin D as well as CD36 and HGF in the cells. Also, the expression patterns showed a linear correlation with the phagocytosis of the Kupffer cells. Therefore, the crude extract PH would evidently enhance the hepatic clearance of the AGEs in view of the increased expression of the cathepsin D, CD36 and HGF genes.

Example 7

Effect of PH on Streptozotocin (STZ) Animal Model

STZ Mice Model

Eight-week-old C57BL/6j mice were chosen in this experiment. The mice were randomly grouped into a normal group (normal mice without STZ-induced DM (Diabetes mellitus)), control STZ group (STZ-induced DM mice), 200 mg/kg/day PH group (STZ-induced DM mice given 200 mg/kg/day of PH) and 1000 mg/kg/day PH group (STZ-induced DM mice given 1000 mg/kg/day of PH). There were 5 mice in each group. To induce DM in the mice, STZ (dissolved in 0.3 mL of 0.1 M citrate buffer, pH 4.5) was intraperitoneally (ip)-injected at a dose of 120 mg/kg on the first day and ip-injected at a dose of 80 mg/kg for the next 3 days. After the final injection of STZ, plasma glucose was monitored every week, and the mice having a high plasma glucose level (>400 mg/dL) were chosen as the STZ-induced mice in following experiments. The PH group mice were fed with PH for 2 month, whereas the control and normal group mice were given normal mouse feeds. Two months later, liver and kidney histopathology was evaluated to determine the drug efficacy.

Urine Albumin Concentration Analysis

Urine was diluted 100× for protein quantification. Bovine Serum Albumin (BSA) standards were serially diluted (2 mg/mL, 1 mg/mL, 500 µg/mL, 250 µg/mL, 125 µg/mL, 61.5 µg/mL, 31.25 µg/mL and 0 µg/mL) for BCA analysis. Following incubation at 37° C. for 30 minutes, O.D. 570 nm absorbance measurements were taken and the standard curve was plotted. A linear regression analysis was conducted to obtain the quantitative standard curve and the $R^2$ value. Total protein concentrations were calculated from the standard curve.

ELISA Test of Urine Albumin

Each well of the 96-well plate was coated with diluted urine sample having fixed total protein content (100 µg total protein in 100 µL PBS) and stored at 4 C overnight. The urine sample was then washed with a wash buffer (0.05% v/v, Tween™ 20 in PBS) for four times before blocking with 5% milk for 2 hours at room temperature. After another four washes with the wash buffer, 50 µL of anti-MSA polyclonal antibody diluted solution (1:1000 in 3% milk) were added into each well and incubated for 2 hours at room temperature. Following six washes with the wash buffer, goat-anti-chicken IgG conjugated with peroxidase diluted solution (1:1000 in PBS-BSA) was added into each well and incubated for 2 hours at room temperature. The bound peroxidase was determined by incubation with 100 µL of 1 mg/mL O-phenylenediamine (in 0.1 M citric acid, pH 5.5) and 5 µL of $H_2O_2$. The reaction was stopped after 10 minutes by adding 2N $NH_2SO_4$ (20 µL/well), and absorbance was measured at a wavelength of 490 nm by an ELISA reader and normalized with the mean absorbance of the normal mice to determine the relative index as shown in Table 4.

TABLE 4

|  | Normal Index ± SD | Control Index ± SD | 200 mg/kg Index ± SD | 1000 mg/kg Index ± SD |
| --- | --- | --- | --- | --- |
| Week 2 | 0.56 ± 0.25** | 1.00 ± 0.17 | 0.81 ± 0.37 | 0.86 ± 0.40 |
| Week 4 | 0.31 ± 0.15** | 1.00 ± 0.20 | 0.88 ± 0.19 | 0.90 ± 0.15 |
| Week 6 | 0.35 ± 0.19*** | 1.00 ± 0.20 | 0.82 ± 0.24 | 0.81 ± 0.24 |
| Week 8 | 0.41 ± 0.22*** | 1.00 ± 0.12 | 0.83 ± 0.19 | 0.67 ± 0.21# |

Data were analyzed by Student's t-test.
*$P < 0.05$,
$P < 0.02$,
**$P < 0.01$,
***$P < 0.001$ compare with control STZ mice (n = 5)

From the results shown in Table 4, the urine albumin level in the mice given 200 mg/kg/day PH or 1000 mg/kg/day PH was significantly lower than the STZ-induced mice of the control group. Accordingly, the above results indicate that the kidney function of the STZ-induced mice was restored when 200 mg/kg/day or 1000 mg/kg/day of the crude extract PH was administered.

Histopathology

Liver and kidney tissues were collected from the mice after being sacrificed, and the peripheral muscle tissue and connective tissue thereof were removed. The tissues were then fixed in 4% paraformadehyde and paraffin-embedded before cutting the tissue into sections, each having a thickness of 5 µm. The tissue sections were deparaffinized in xylene and rinsed in gradient ethanol (100% ethanol, 95% ethanol, 80% ethanol) before staining with hematoxylin and eosin (H&E).

Figure 4A:
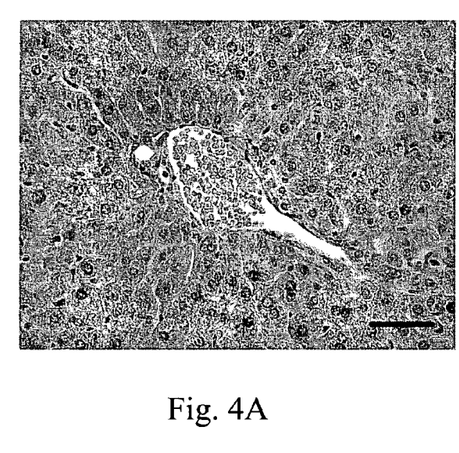
FIGS. 4A through 4D are microscopic images showing different liver histology of an STZ induced diabetes mouse, each image having a magnification of 400× and the scale bars represent 50 µm.
Figure 4B:
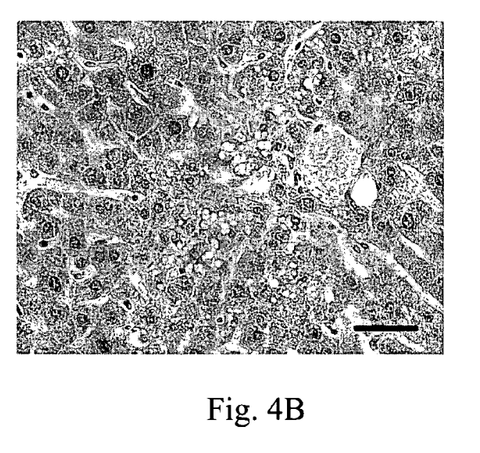
Figure 4C:
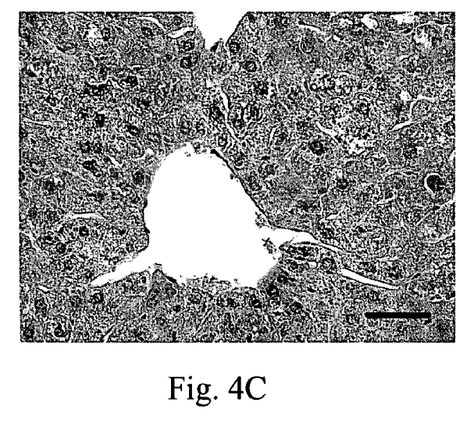
Figure 4D:
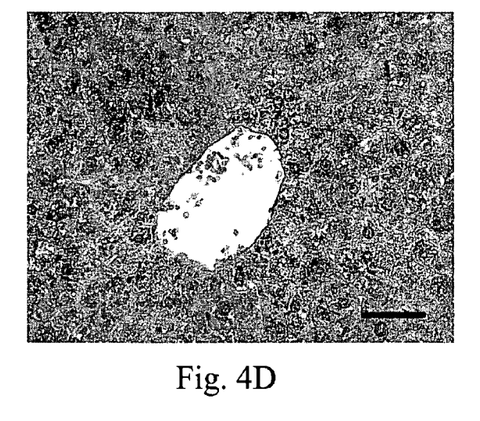

Next, the liver tissue sections prepared as described above were observed under light microscopy. FIG. 4A shows a healthy liver tissue section with hepatocytes from the normal mouse. Referring to FIG. 4B, a number of vesicles were found in the liver tissue section of the STZ-induced mice, indicating occurrence of fatty degeneration in the hepatocytes. In the STZ-induced mice given different dosages of PH, the liver tissue was repaired and prevented from the damage in a dose dependent manner as shown in FIGS. 4C and 4D, although slight glycogen accumulations may still be observed in these liver tissue sections.

Figure 5A:
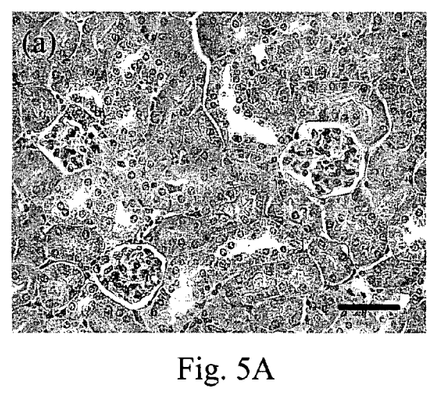
FIGS. 5A through 5D are microscopic images showing different kidney histology of an STZ induced diabetes mouse, each image having a magnification of 400× and the scale bars represent 50 µm.
Figure 5B:
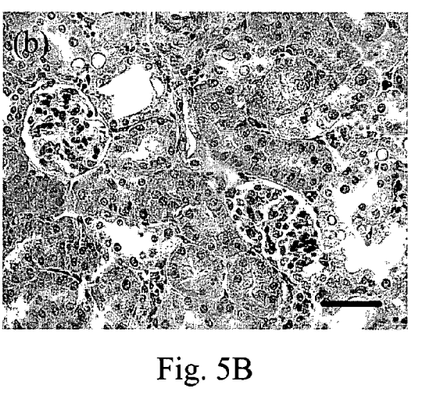
Figure 5C:
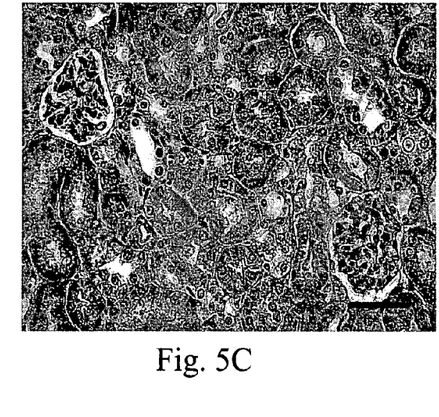
Figure 5D:
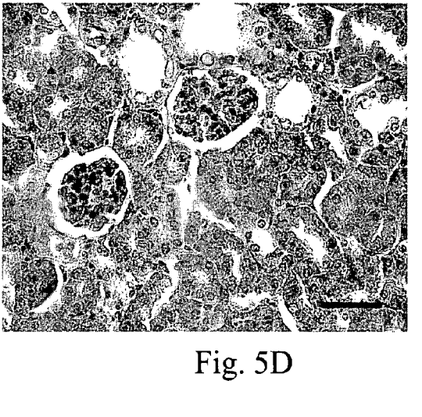

FIG. 5A shows a healthy kidney tissue section with glomeruli from the normal mouse. In FIG. 5B, the kidney tissue section of the STZ-induced mice shows damaged glomeruli to contrast with the health kidney section of the normal mouse. As the STZ-induced mice were given different dosages of PH, the kidney tissue was repaired and prevented from the damage in a dose dependent manner as shown in FIGS. 5C and 5D, although a few damaged glomeruli may still be observed in these kidney tissue sections.

Example 8

Effect of PH on AGE-BSA Mice Model

Mice Serum Preparation

Whole blood samples were collected from mice by orbital bleeding every two weeks. The blood was allowed to clot for at least 2 hours at room temperature and then centrifuged to obtain the serum. The serum was stored at −20° C. until assayed.

Serum Albumin Purification

Mice serum was kept at 0 to 4° C. The precipitate was removed by centrifugation at 9,000 g for 15 minutes at the same temperature. The supernatant was adjusted to pH 6.9 with an equal volume of 50% ethanol (pH 6.7) and left standing for 10 minutes before further centrifuging at 9,000 g for 15 minutes in order to obtain the fractions I, II and III of the supernatant.

The fractions I, II and III of the supernatant were titrated again with a half volume of 70% ethanol (pH 5.8) to adjust to pH 5.8 and left standing for 10 minutes before centrifuging at 9,000 g for 15 minutes in order to obtain the fraction IV precipitate. The fraction IV supernatant was adjusted to pH 4.8, followed by standing on ice at −5° C. for 60 minutes, and centrifuging at 9,000 g for 10 minutes in order to obtain the fraction V. The fraction V was frozen and dried for weight analysis.

AGE-MSA Preparation 0.1 g/ml MSA (mouse serum albumin) and 180 mg/ml glucose were separately dissolved in sodium phosphate buffer (pH 7.4). The solution was filtered with a 0.22 µm sterilized filter. 5 mL of the solution were added to a 15 mL test tube which was sealed with parafilm and incubated at 37° C. in the dark. After 8 weeks of storage, the solution was dialyzed 3 or 4 times with distilled water (1/100, v/v) at 4° C. to completely remove the glucose. The resulting AGE-MSA was filtered with the 0.22 μm sterilized filter, lyophilized into powder and quantified before re-dissolving and storing at −20° C.

AGEs Mice Model

Ten weeks old C57BL/6J mice were randomly grouped into a normal group (normal mice without any injection), MSA control group (mice injected with MSA), 200 mg/kg/day PH group (AGE-injected mice given 200 mg/kg/day of PH), 1000 mg/kg/day PH group (AGE-injected mice given 1000 mg/kg/day of PH) and AGE-MSA control group (mice injected with AGE-MSA to induce diabetic vascular complications). There were 5 mice in each group. The mice were injected intravenously with AGEs-MSA in a volume of 200 μL. Mice were administered with eight intravenous injections, each injection containing 4 mg/time/mice control MSA or AGE-MSA (2 times/week for 4 weeks). The mice were given mouse feeds containing PH at different doses from day 15. After two months, mice were sacrificed and their liver and kidney were removed for histopathology.

Figure 6A:
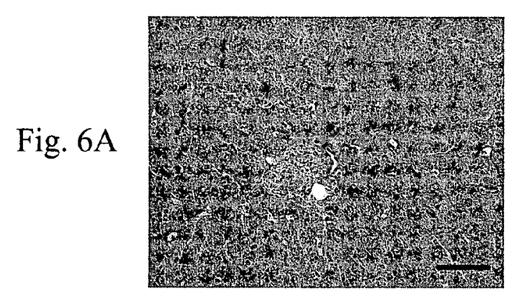
FIGS. 6A through 6E are microscopic images showing different liver histology of an AGEs injected mouse, each image having a magnification of 640× and the scale bars represent 20 µm.
Figure 6B:
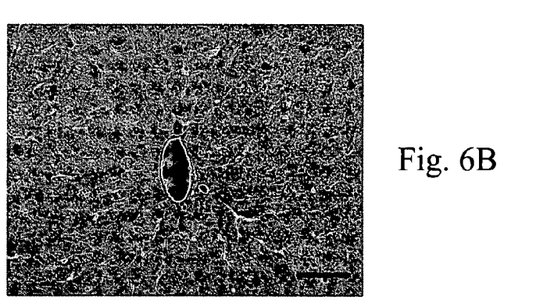
Figure 6C:
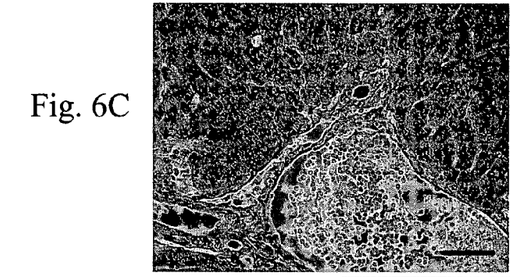
Figure 6D:
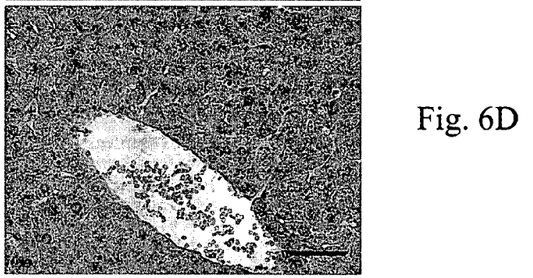
Figure 6E:
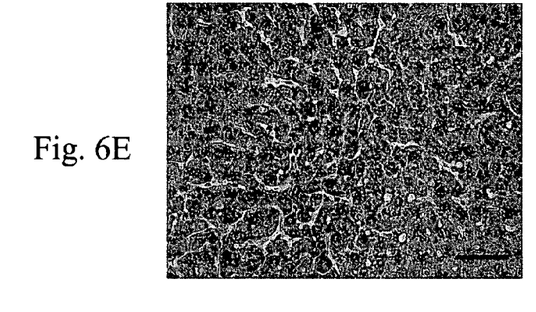
Figure 7A:
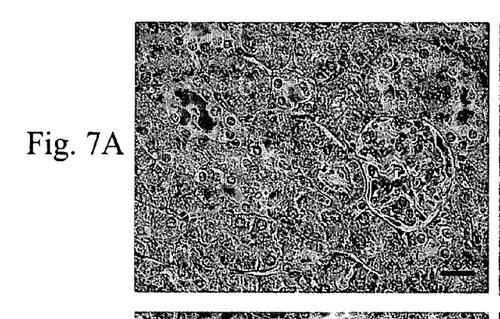
FIGS. 7A through 7E are microscopic images showing different kidney histology of an AGEs injected mouse, each image having a magnification of 640× and the scale bars represent 20 µm.
Figure 7B:
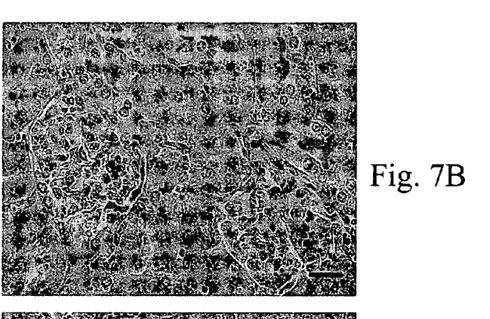
Figure 7C:
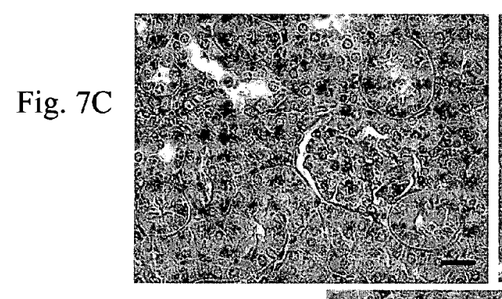
Figure 7D:
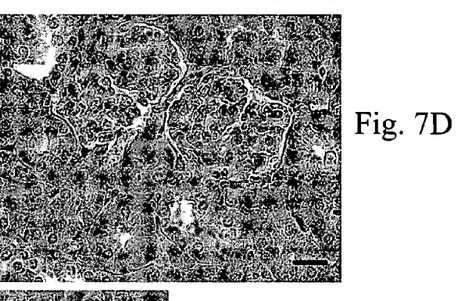
Figure 7E:
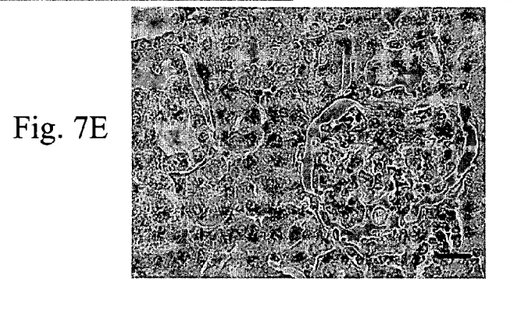

Referring to FIG. 6E, the hepatocytes were irregular in shape with accumulation of extracellular matrix (ECM) in the liver tissue section of the mice in the AGE-MSA control group, indicating a large scale of the hepatocytes were damaged. In contrast, no such damage was observed in the liver tissue section from the mice given the crude extract PH (FIGS. 6C and 6D). Therefore, it has been demonstrated that the crude extract PH can minimize the liver damage caused by the AGE-MSA. In the kidney tissue section of the normal or the MSA-control mice, the glomeruli are intact with no increase of extracellular matrix (ECM) (FIGS. 7A and 7B). In contrast, the glomeruli were clearly damaged and hypertrophied as observed in the kidney tissue section from the mice injected with AGE-MSA (FIG. 7E). As the AGE-injected mice were given different dosages of PH (200 mg/kg/day PH and 1000 mg/kg/day PH), the kidney tissue was repaired and restored as such to resemble the kidney of the normal mice.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for treating liver or kidney tissue damage in a diabetic vascular complication subject triggered by an excessive accumulation of an advanced glycation end-product (AGE) comprising administering to a subject in need thereof a therapeutically effective amount of an alcohol and acetic acid extract product of a *Dioscorea alata* L. cv. Phyto.

2. The method according to claim 1, wherein the extract product is administered orally.

3. The method according to claim 1, wherein the extract product is prepared by a process comprising:

(a) mixing a tuber of the *Dioscorea alata* L. cv. Phyto with an alcohol-based solvent in the presence of acetic acid to obtain an extract composition;
(b) subjecting the extract composition obtained in step (a) to a separating treatment to obtain a soluble fraction; and
(c) removing the solvent from the soluble fraction obtained in step (b) to obtain the extract product.

4. The method according to claim 3, wherein the alcohol-based solvent is a methanol-based solvent, an ethanol-based solvent, or a mixture thereof.

5. The method according to claim 1, wherein the extract product is prepared by a process comprising:

(a) immersing a tuber of the *Dioscorea alata* L. cv. Phyto in a 1% acetic acid solution;
(b) grinding the acetic acid-treated tuber;
(c) lyophilizing the ground and acetic acid-treated tuber to produce a ground, lyophilized and, acetic acid-treated tuber;
(d) mixing at least a portion of the ground, lyophilized and acetic acid-treated tuber of (c) with an alcohol-based solvent in the presence of an about 1% acetic acid solution to obtain an extract composition;
(e) subjecting the extract composition obtained in (d) to a separating treatment to obtain a soluble fraction; and
(f) removing the solvent from the soluble fraction obtained in (e) to obtain the extract product.

6. The method according to claim 5, wherein the alcohol-based solvent is a methanol-based solvent, an ethanol-based solvent, or a mixture thereof.

* * * * *

SEQUENCE LISTING

```
<160> NUMBER OF SEQ ID NOS: 9

<210> SEQ ID NO 1
<211> LENGTH: 10
<212> TYPE: DNA
<213> ORGANISM: Artificial
<220> FEATURE:
<223> OTHER INFORMATION: primer

<400> SEQUENCE: 1
aggtgaccgt                                                          10

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
gactacctca tgaagatcct                                               20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
ccacatctgc tggaaggtgg                                               20

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
```

-continued

```
ggatcgaaat cgaccttaaa g                                              21

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
tagctggctt gaccaatatg tt                                             22

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
cgtcttgctg ctcattctcg                                                20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
ccaccagaag agatgtccct                                                20

<210> SEQ ID NO 8
<211> LENGTH: 21
<212> TYPE: DNA
<213> ORGANISM: Artificial
<220> FEATURE:
<223> OTHER INFORMATION: primer

<400> SEQUENCE: 8
ccatgaattt gacctctatg a                                              21

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
ctgaggaatc tcacagactt c                                              21
```